United States Patent
Tamura et al.

(10) Patent No.: US 6,417,295 B1
(45) Date of Patent: Jul. 9, 2002

(54) METHOD AND APPARATUS FOR DETECTING AGGLOMERATES

(75) Inventors: Mitsuru Tamura; Koji Takimiya, both of Sodegaura; Tsutomu Konaka, Ichihara, all of (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/575,248

(22) Filed: May 22, 2000

(30) Foreign Application Priority Data

Dec. 10, 1999 (JP) .......................... 11-351843

(51) Int. Cl.⁷ .................................................. C08F 2/34
(52) U.S. Cl. ..................... 526/59; 526/901; 526/68; 526/60; 73/661; 73/781; 422/139
(58) Field of Search ........................... 526/68, 901, 60, 526/59; 73/661, 781; 422/139

(56) References Cited

FOREIGN PATENT DOCUMENTS

| JP | 06-136013 | 5/1994 |
| JP | 10-36447 | 2/1998 |
| JP | 10036447 A | * 2/1998 |

* cited by examiner

*Primary Examiner*—David W. Wu
*Assistant Examiner*—William K Cheung
(74) *Attorney, Agent, or Firm*—Sughrue Mion, PLLC (57) ABSTRACT

Agglomerates 20 in a mixed phase container 1 are detected by measuring strain in a detecting rod 50 disposed in the mixed phase container 1 in which a mixed phase of gas and powders is formed. The detecting rod 50 is disposed at an insertion angle θ in the range from 20 degrees to 70 degrees with relation to the flow of gas and powders.

10 Claims, 11 Drawing Sheets

FIG. 6
load-displacement graph

METHOD AND APPARATUS FOR DETECTING AGGLOMERATES

BACKGROUND OF THE INVENTION

1. Field of the Invention

The present invention relates to a method and apparatus for detecting agglomerates formed in a mixed phase container such as a fluidized-bed olefin polymerization reactor container, and to a method and apparatus for fluidized-bed olefin polymerization.

2. Description of the Related Art

It is well known in the art that a method of radiation is being used for detecting agglomerates formed in a mixed phase container, such as a fluidized-bed olefin polymerization reactor container (refer to Japanese Patent Publication No.62-28961). In the radiation method, a radiation source is placed in the center of the container and a plurality of radiation detectors are disposed around the container. In order to detect the existence and the size of agglomerates, the detectors detect density fluctuations in the mixed phase between the radiation source and the detectors by using the radiation.

Another method for detecting agglomerates in the mixed phase container, shown in Japanese Laid-open Patent Publication No.4-361150, employs an electrostatic capacitance detecting method. Means for detecting electrostatic capacitance is disposed on the inner wall of the mixed phase container. This method is based on detecting fluctuations of electrostatic capacitance, since the density (dielectric constant) of agglomerates is greater than that of the mixed phase. When the agglomerates as gel-like are formed and attached on the wall in the mixed phase container, the detecting means detects fluctuations in the electrostatic capacitance thereof. Therefore, the detecting means is able to monitor the state of agglomerates by measuring the amount of fluctuations in electrostatic capacitance.

Further, another method for detecting agglomerates employs a detecting rod having a strain detecting means in the mixed phase container, as shown in Japanese Laid-open Patent Publication No.10-36447. According to this method, it is possible to detect the existence and the size of agglomerates formed in the mixed phase container by detecting an amount of the strain generated in the detecting rod when agglomerates collide with the detecting rod.

However, the method described above employing radiation to detect agglomerates requires special attention. For example, a fluidized-bed olefin polymerization reactor container is generally an enormous container of roughly cylindrical shape having a diameter of several meters and a height of several tens of meters. A worker must enter the container to remove the blockage when blockage occurs, or to perform the inspections at periodic inspections. Accordingly, since a radiation source is present in the container, sufficient considerations must be made to ensure the safety of workers performing such operations.

While the method employing an electrostatic capacitance detecting means to detect agglomerates is suitable for detecting agglomerates adhered to the inner walls of the container and has no problem related to safety, the method is not sufficiently precise for detecting agglomerates which are moving within the container. Further, since the difference between the density of small agglomerates and that of normal olefin polymer product is small, this method is not sufficient even for detecting agglomerates adhered to the inner walls of the container.

The method of detecting agglomerates using a strain detecting device does not have the problems described above. However, in this method, it is essential that the agglomerates effectively collide with the detecting rod. Since the agglomerates formed in the container move along with the flow of gas and powders such as products of the olefin polymer and/or catalysts in the mixed phase, it is necessary to know beforehand how gas and powders in the mixed phase will flow. Or else, agglomerates will not collide with the detecting rod with an effective force, thereby greatly lowering the sensitivity of detection.

If the detecting rod and the direction in which gas and powders flow form a right angle or obtuse angle, agglomerates moving along with the flow of gas and powders may get caught and accumulate on the part of the detecting rod facing with the flow. If agglomerates adhere to the detecting rod in this way, not only it is impossible to precisely detect the agglomerates, but also the accumulating agglomerates actually block detection of other agglomerates in the container. As the agglomerates accumulate further, it is very likely that the accumulation will obstruct fluidization in the container and promote further agglomeration.

SUMMARY OF THE INVENTION

The present invention has been made in view of the above drawbacks. It is an object of the present invention to provide a safe method and apparatus capable of detecting even small agglomerates with a high degree of precision and sensitivity and without obstructing fluidization within the mixed phase container. It is another object of the present invention to provide a method and apparatus for fluidized-bed olefin polymerization.

According to an aspect of the present invention, there is provided a method for detecting agglomerates in a mixed phase container by measuring strain in a detecting rod disposed in the mixed phase container in which a mixed phase of gas and powders is formed, wherein the detecting rod is disposed at an insertion angle in the range from 20 degrees to 70 degrees, preferably from 25 degrees to 50 degrees, with relation to the flow of gas and powders. This method can prevent the agglomerates formed in the mixed phase container from accumulating on the part of the detecting rod facing with the flow.

According to another aspect of the present invention, there is provided a method for detecting agglomerates, wherein a distributor plate specially designed to swirl gas and powders above the plate (referred to as distributor plate hereinafter) is disposed on the bottom of the mixed phase container for diffusing the gas in a horizontal direction, and the detecting rod is positioned at a predetermined height above the distributor plate. This method can control the flow of gas and powders within the mixed phase container, thereby effectively forcing the agglomerates to collide with the detecting rod.

According to another aspect of the present invention, there is provided an apparatus for detecting agglomerates in a mixed phase container by strain detecting means in a detecting rod disposed in the mixed phase container in which a mixed phase of gas and powders is formed, wherein the detecting rod is disposed at an insertion angle in the range from 20 degrees to 70 degrees with relation to the flow of gas and powders. This arrangement can prevent the agglomerates formed in the mixed phase container from accumulating on the part of the detecting rod facing with the flow more effectively.

According to another aspect of the present invention, there is provided an apparatus for detecting agglomerates, wherein a distributor plate is disposed on the bottom of the mixed phase container for diffusing the gas in a horizontal direction, and the detecting rod is positioned at a predetermined height above the distributor plate. This arrangement can control the flow of gas and powders within the mixed phase container, thereby effectively forcing the agglomerates to collide with the detecting rod.

According to another aspect of the present invention, there is provided a fluidized-bed olefin polymerization reactor wherein a mixed phase of gas and powders is formed, the reactor comprising an apparatus for detecting agglomerates in the mixed phase, the apparatus having a detecting rod for measuring strain when the agglomerates collide thereto, wherein the detecting rod is disposed at an insertion angle in the range from 20 degrees to 70 degrees with relation to the flow of gas and powders.

According to another aspect of the present invention, there is provided an olefin polymerization method, comprising: detecting agglomerates in a mixed phase container by measuring strain in a detecting rod disposed in the mixed phase container in which a mixed phase of gas and powders is formed, wherein the detecting rod is disposed at an insertion angle in the range from 20 degrees to 70 degrees with relation to the flow of gas and powders; and removing the agglomerates from the mixed phase container.

According to another aspect of the present invention, there is provided a method for manufacturing an olefin polymer, said method comprising: detecting agglomerates in a mixed phase container by measuring strain in a detecting rod disposed in said mixed phase container in which a mixed phase of gas and powders is formed, wherein said detecting rod is disposed at an insertion angle in the range from 20 degrees to 70 degrees with relation to the flow of the gas and powders; and removing said agglomerates from said mixed phase container.

The above and other objects, features, and advantages of the present invention will be apparent from the following description when taken in conjunction with the accompanying drawings which illustrates preferred embodiments of the present invention by way of example.

DETAILED DESCRIPTION OF THE PREFERRED EMBODIMENTS

An embodiment according to the present invention will be described below with reference to the accompanying drawings. In this embodiment, a fluidized-bed olefin polymerization reactor container is used as a mixed phase container.

Figure 1:
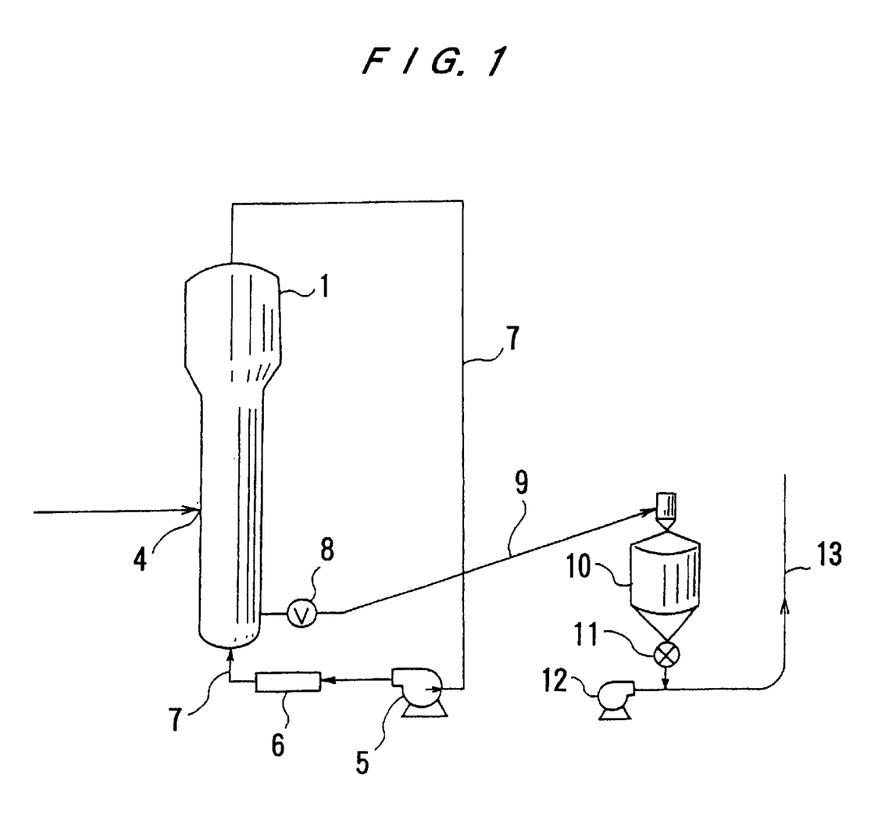
FIG. 1 is a schematic diagram showing a fluidized-bed olefin polymerization reactor container and its peripheral pipelines, according to an embodiment of the present invention.

FIG. 1 is a schematic diagram showing a fluidized-bed olefin polymerization reactor container and its peripheral pipelines. A mixed phase of gas and powders is formed and fluidized in a fluidized-bed olefin polymerization reactor container 1, which serves as a mixed phase container. A polymerization reaction occurs in such a state. The pressure in the fluidized-bed olefin polymerization reactor container 1 is approximately in the range from 1 to 3 MPa and the temperature approximately in the range from 70 to 100° C.

A catalyst and an olefin gas such as ethylene gas are supplied through an inlet 4 into the fluidized-bed olefin polymerization reactor container 1. A circulating gas constantly circulates via a gas line 7 by a circulating gas compressor 5. A heat exchanger 6 is provided along the path of the circulating gas for adjusting the temperature of the circulating gas.

A polymerization reaction occurred in the fluidized-bed olefin polymerization reactor container 1 generates such products as powdered polyethylene, polypropylene, or the like. These products pass through a discharge valve 8 and a discharge line 9 into a primary silo 10, in which the products are stored temporarily. The products are conveyed into nitrogen-compressor line 13 by a rotary valve 11 and delivered to a desired location by wind-force of nitrogen-compressor blower 12.

Figure 2:
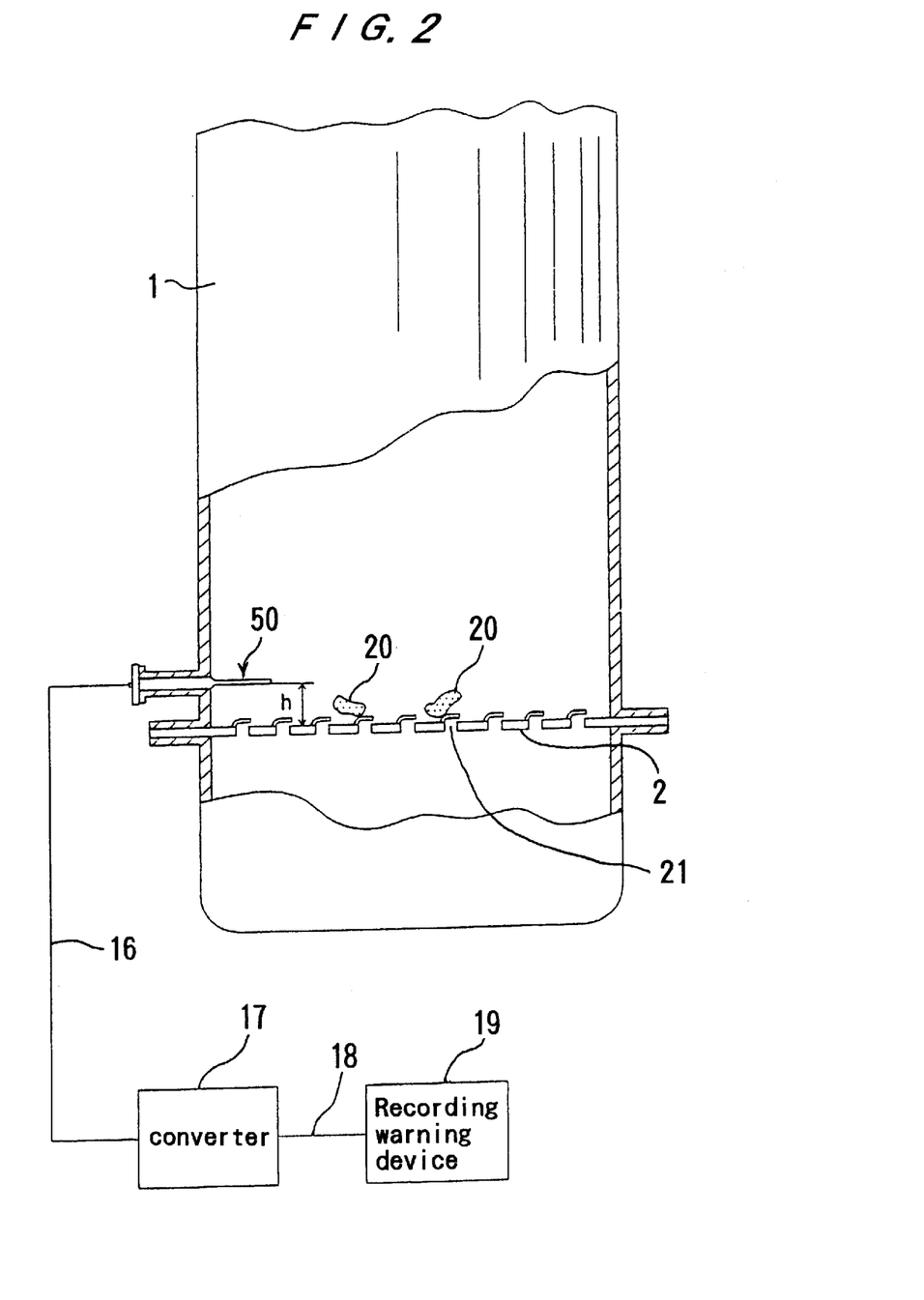
FIG. 2 is an enlarged diagram showing the lower portion of the fluidized-bed olefin polymerization reactor container according to an embodiment of the present invention.

FIG. 2 is an enlarged diagram showing the lower portion of the fluidized-bed olefin polymerization reactor container 1 with part of the container 1 cut out to illustrate its internal construction. The circulating gas supplied from the lower portion of the fluidized-bed olefin polymerization reactor container 1 flows upward from a plurality of opening holes 21 formed on the distributor plate 2 to form a mixed phase of gas and powders in the fluidized-bed olefin polymerization reactor container 1, in which a polymerization reaction occurs.

During this process, agglomerates 20 are formed in nodules due to variations in the state of the mixed phase. The process of this formation of agglomerates is not completely elucidated yet.

While the formed agglomerates 20 remain small, agglomerates circulate in the mixed phase in the floating state along with the flow of powders in the mixed phase. As the agglomerates 20 grow larger, however, agglomerates are no longer fluidized together with the powders and begin to settle in the mixed phase. Such agglomerates 20 generally accumulate near the distributor plate or else move irregularly due to the force of the circulating gas diffused from the opening holes on the distributor plate.

In order to move these large agglomerates 20 over the distributor plate 2, the inventors gave directivity to the circulating gas diffused from the opening holes 21, and developed a distributor plate that forces the flow of gas and powders to move over the distributor plate 2 in a circular direction by orienting the opening holes 21 in the same circular direction (refer to Japanese Laid-open Patent Application Publication No.5-136013). In the present embodiment, this distributor plate is used as the distributor plate 2.

Figure 3:
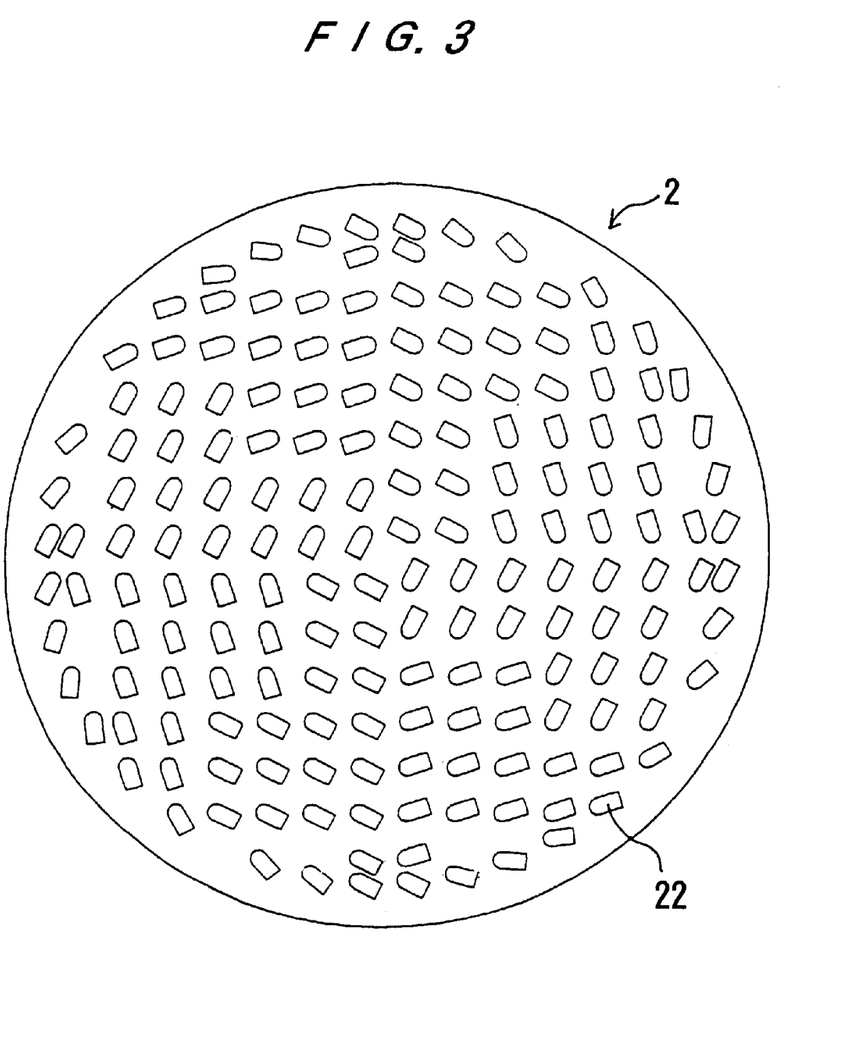
FIG. 3 is a plan view of the distributor plate in FIG. 2.

As shown in FIG. 3, the opening holes 21 through which the gas is diffused are formed in concentric circles on the distributor plate 2, and streamlined caps 22 are disposed on top of the opening holes 21. With this construction, the gas is diffused in a horizontal direction from the opening holes 21 on the distributor plate 2. In FIG. 3, the gas flows in the counterclockwise direction.

Accordingly, the large agglomerates described above can be moved in a specific circular direction (counterclockwise in FIG. 3) along the gas flow over the distributor plate 2. As the behavior of agglomerates within the mixed phase is dependent not only on the size of the agglomerates but also on operating conditions, such as rate of gas flow, it is possible to move even large agglomerates with a high rate of gas flow.

As shown in FIG. 2, a detecting rod 50 is disposed inside the fluidized-bed olefin polymerization reactor container 1, and comprises an apparatus for detecting agglomerates 20 formed by the adherence of each olefin polymer. The detecting rod 50 will be described below in detail.

The detecting rod 50 is supported like a cantilever with one end fixed to the side wall of the fluidized-bed olefin polymerization reactor container 1 and the other projecting freely into the reactor container 1. The detecting rod 50 is disposed at a predetermined height above the distributor plate 2.

Figure 4:
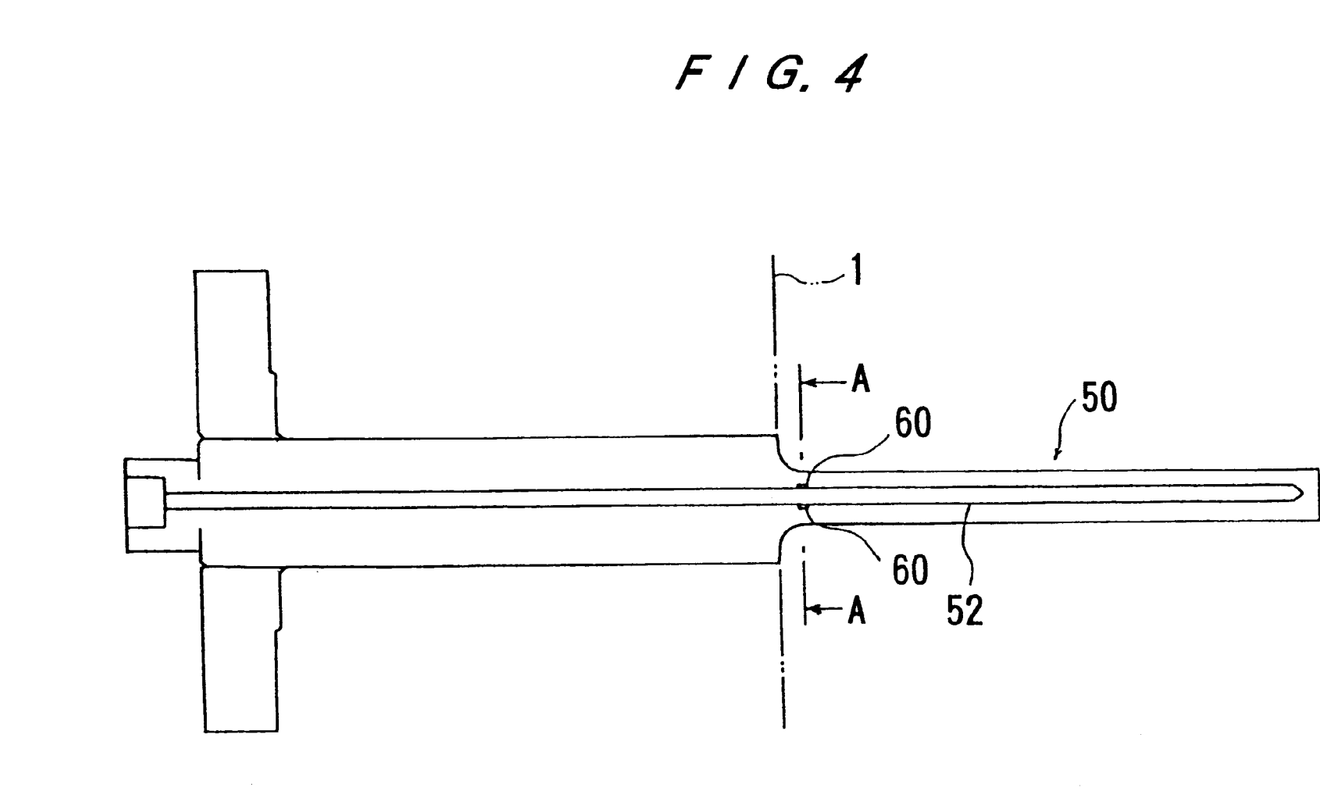
FIG. 4 is a side cross-sectional view of the detecting rod in FIG. 2.
Figure 5:
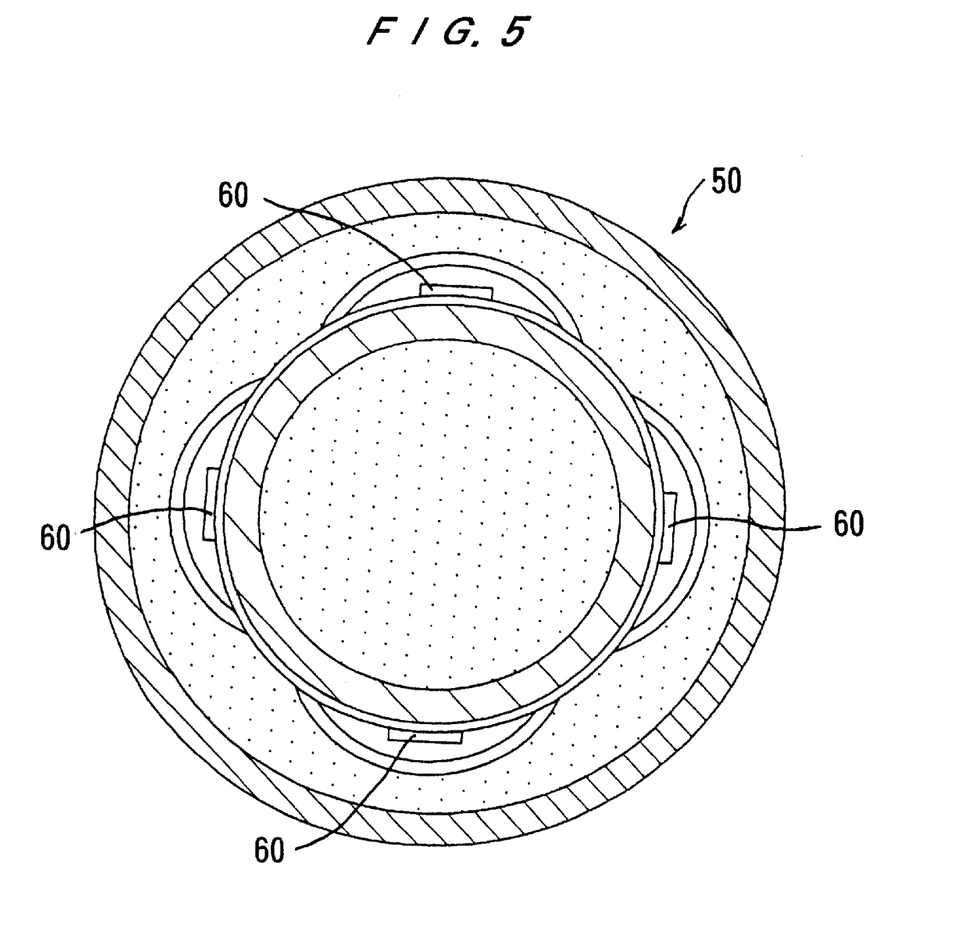
FIG. 5 is an enlarged cross-sectional view taken along a line A—A in FIG. 4.

As shown in FIGS. 4 and 5, strain detecting means (strain gauges) 60 are disposed at four locations, that is, at the top, bottom, left, and right with the cross-section of the detecting rod 50. Output signals from each of the strain detecting means 60 are inputted via a cable 16 into a converter 17 and converted to the current signals ranging from 4 to 20 mA thereby. The signals are transferred via a cable 18 into a recording warning device 19 to be monitored.

As the agglomerates 20 circulate along with the mixed phase, the agglomerates 20 collide with the detecting rod 50 to generate strain. The strain detecting means 60 measure the amount and frequency of the strain to detect the existence and size of the agglomerates 20 in the reactor container.

More specifically, the strain gauges 60 are provided with element wires having a resistance R, shown below.

$$R=\rho l/d^2$$

Here, $\rho$ is resistivity, l is the length of the element wire, and d is the diameter of the element wire.

When agglomerates 20 collide with the detecting rod 50, the detecting rod 50 expands and contracts, causing the lengths l of the element wires in the strain gauges 60 to change. As a result, the resistance R of the element wires also changes. Accordingly, the degree to which agglomerates 20 are formed can be understood from the amount of change detected in the resistance R. Further, since the strain gauges 60 are disposed at four positions, that is, at the top, bottom, left, and right with the cross-section of the detecting rod 50, as described above, one of the detecting rods 50 can measure the strain, regardless of the direction in which the agglomerates 20 collide with the detecting rod 50.

As described above, the detecting rod 50 is mounted in the side of the fluidized-bed olefin polymerization reactor container 1 at a predetermined height above the distributor plate 2. This predetermined height h (refer to FIG. 2) may be set at a height to enable detection of agglomerates 20 of a size that can fit through the discharge valve 8, for example, ranging from about 5 to about 15 cm.

Figure 6:
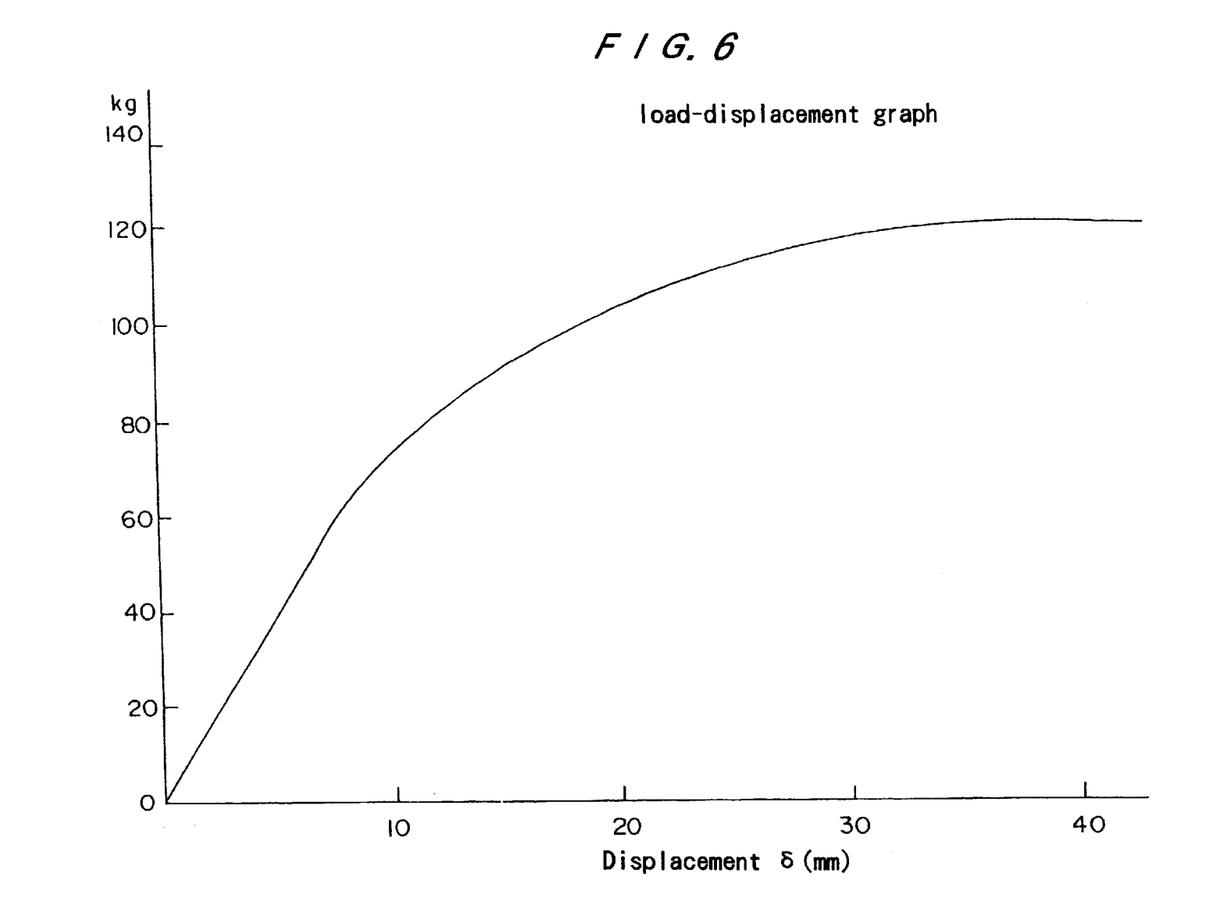
FIG. 6 is a graph showing the strain in the detecting rod in relation to load acting on the rod.

FIG. 6 is a graph illustrating the relationship between the load and the strain (displacement δ) when a load is applied on the detecting rod 50. The horizontal axis represents the strain, while the vertical axis represents the load. In a normal state, a certain extent of the load is applied to the detecting rod 50 by the swirling flow in the fluidized-bed olefin polymerization reactor container 1, but the amount of the load is very small and the detecting rod 50 is stable. As the load increases, the strain also grows larger. The load can be determined based on the amount of strain with reference to the graph in FIG. 6.

If agglomerates 20 are formed in the fluidized-bed olefin polymerization reactor container 1 and collide with the detecting rod 50, then the load on the detecting rod 50 increases abruptly and the strain generated in the detecting rod 50 changes. It is possible to detect both the existence and size of agglomerates by the amount of this change in the strain.

Figure 7:
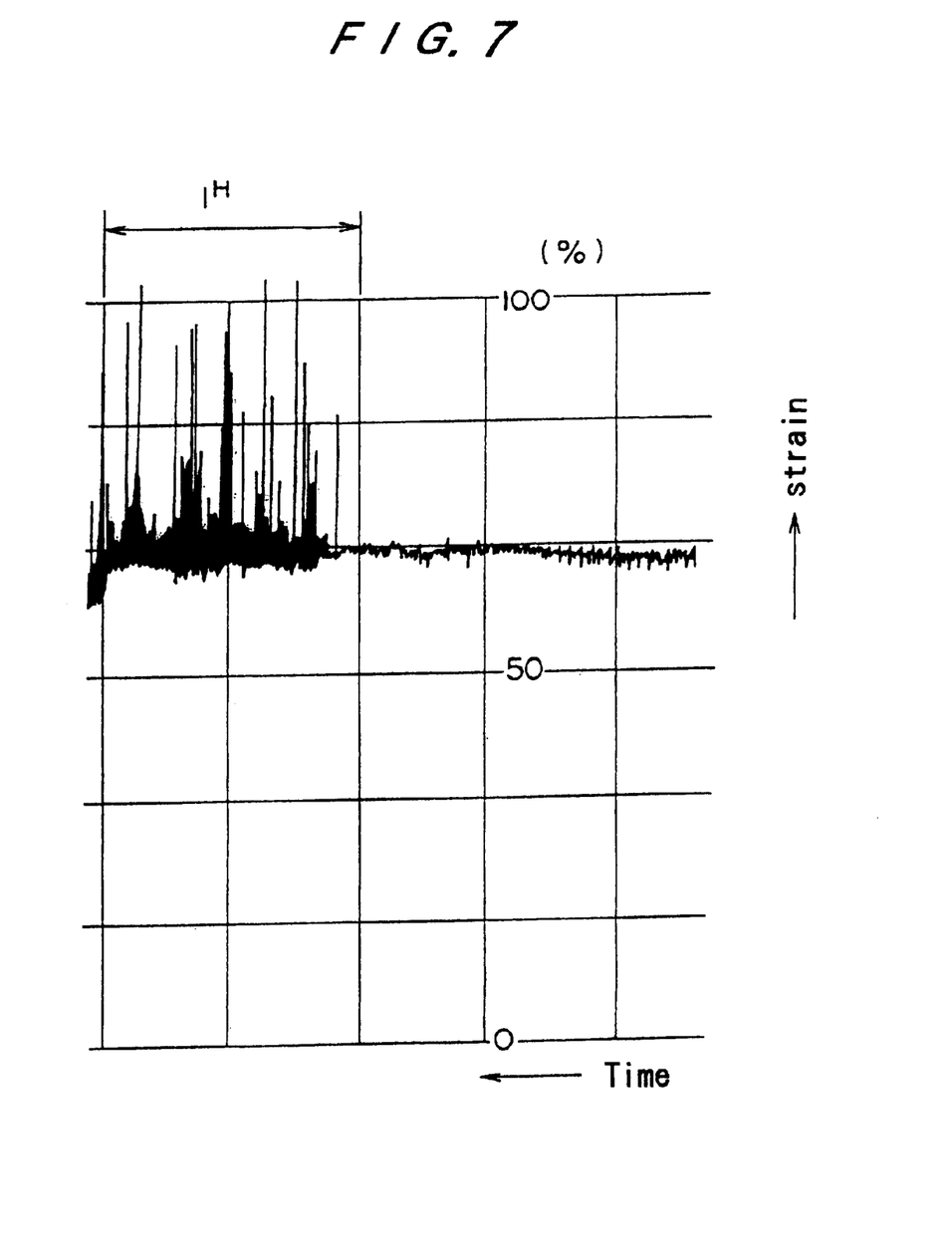
FIG. 7 is a graph showing the amount of strain measured in the detecting rod during an experiment in which the detecting rod was disposed.
Figure 8:
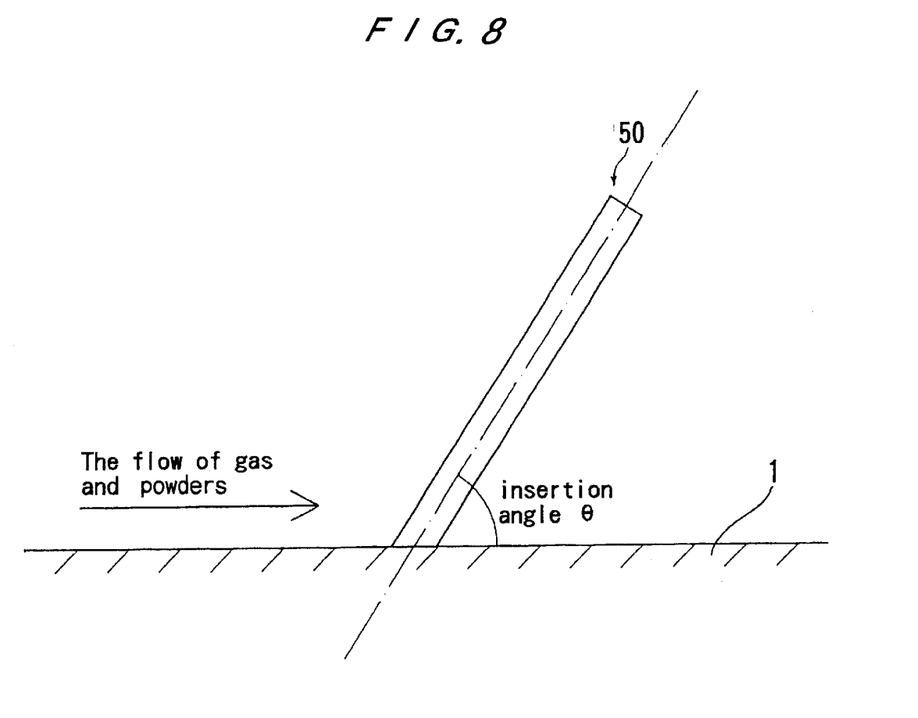
FIG. 8 is an explanatory diagram illustrating the insertion angle of the detecting rod.

FIG. 7 shows a result of an actual experiment in which the detecting rod 50 was disposed at the insertion angle, that is, the angle θ formed by the detecting rod 50 and the direction of the swirling gas and powders (refer to FIG. 8), of 90 degrees, and agglomerates 20 formed in the fluidized-bed olefin polymerization reactor container 1 were detected. In FIG. 7, the horizontal axis represents time (one graduation signifies 30 minutes), while the vertical axis represents strain. As shown in the graph in FIG. 7, after a certain time has elapsed, considerably large strains occur in the detecting rod 50 at regular intervals of about 6 minutes. Consequently, it indicates that agglomerates 20 have been formed in the fluidized-bed olefin polymerization reactor container 1 and that the agglomerates 20 circulate in the reactor container 1 with a period of about 6 minutes.

In this way, the state of agglomerates 20 formed in the fluidized-bed olefin polymerization reactor container 1 can be detected by changes in the strain generated in the detecting rod 50. Further, the formation and the size of agglomerates 20 can be detected by the magnitude and period of strains after sudden change. Certainly, even if a distributor plate is used as described above, powders or agglomerates may not move strictly horizontally, but may move vertically as well. However, since the strain gauges 60 are disposed at four positions, as described above, it is still possible to detect vertically moving powders or agglomerates.

Figure 9:
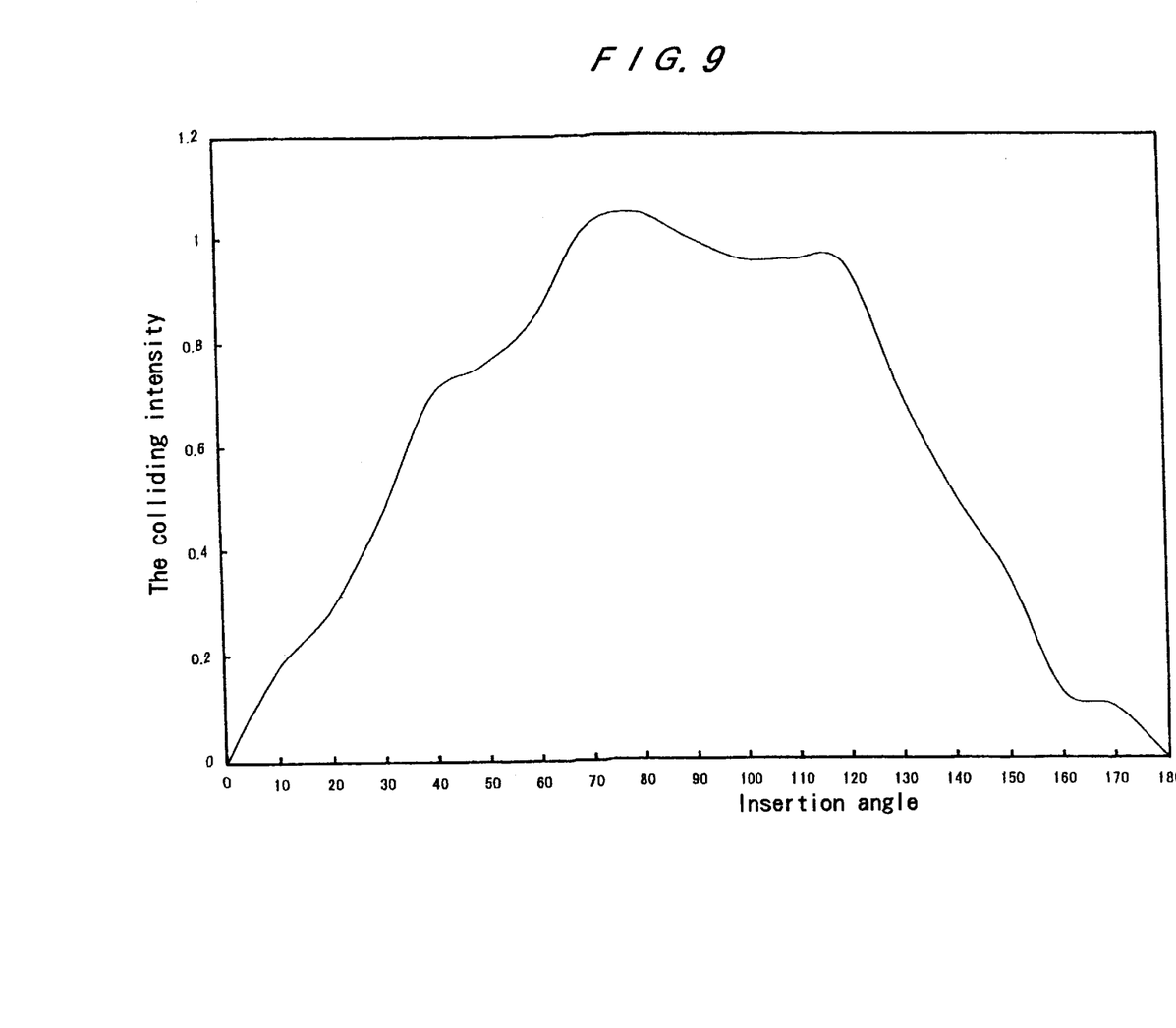
FIG. 9 is a graph showing the relationship between the insertion angle and the colliding intensity (assuming that the value at the insertion angle θ of 90 degrees is 1.0)
Figure 10:
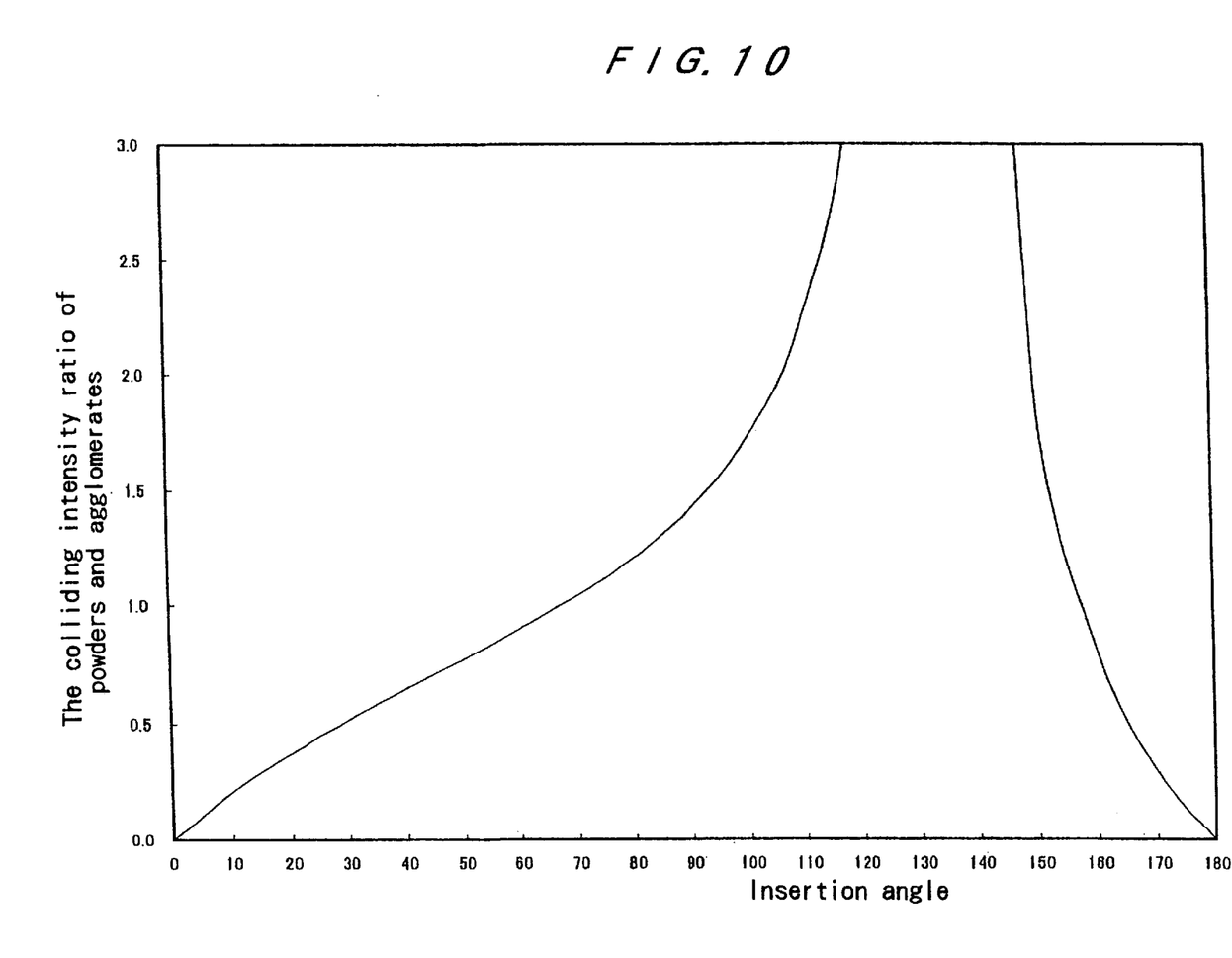
FIG. 10 is a graph showing the relationship between the insertion angle and the colliding intensity ratio of powders and agglomerates.

FIG. 9 shows a comparison of colliding intensity (detection sensitivity) when agglomerates 20 collide with the detecting rod 50 for various insertion angles θ of the detecting rod 50 using a distributor plate as a distributor plate 2. FIG. 10 shows a comparison of the ratio of powders colliding intensity to agglomerate colliding intensity (equivalent to the resolution at the time of detection) under the condition in FIG. 9.

FIG. 9 shows the ratio of colliding intensity when the detecting rod 50 is at a given insertion angle θ to the colliding intensity when the detecting rod 50 is inserted at an insertion angle θ of 90 degrees (assuming that the value at the insertion angle of 90 degrees is 1.0). From the graph shown in FIG. 9, the insertion angle θ to obtain a colliding intensity ratio of 30% or higher is approximately in the range from 20 degrees to 160 degrees. A certain level of detecting sensitivity can be expected to be obtained within the above range.

In FIG. 10, the ratio of colliding intensity between powders and agglomerates 20 represents the ratio of signal strength (S/N ratio) of at a normal state (in which agglomerates are not colliding with the detecting rod) to at a colliding state (in which agglomerates are colliding with the detecting rod).

From two graphs shown in FIGS. 9 and 10, when a detecting rod 50 is inserted at an insertion angle θ ranging from 20 degrees to 160 degrees, a certain level of detecting sensitivity and resolution can be obtained.

Figure 11:
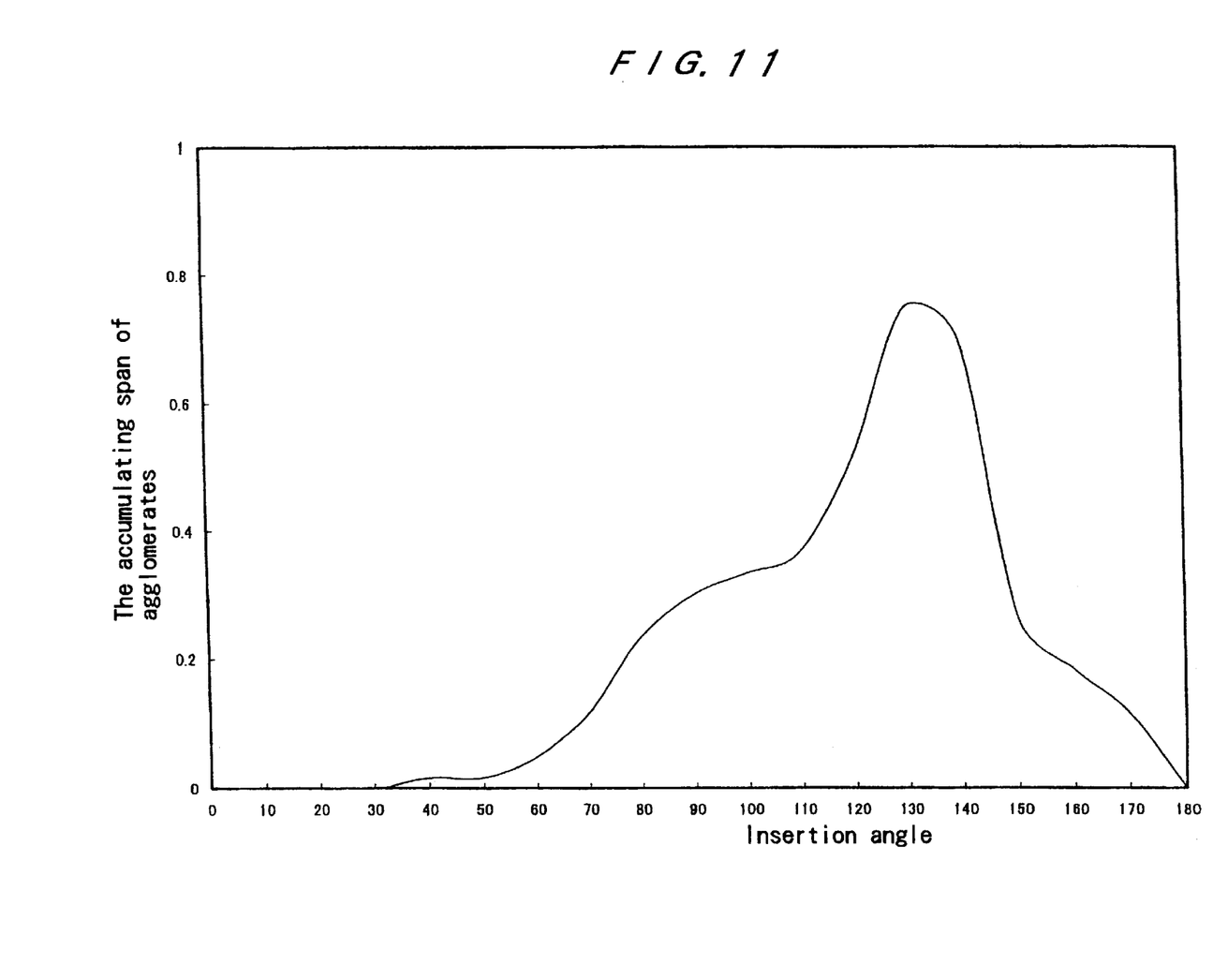
FIG. 11 is a graph showing the relationship between the insertion angle and the accumulating span of agglomerates.

However, data from the experiments also indicate that the agglomerates 20 occasionally adhered to and accumulated on the part of the detecting rod 50 facing with the flow. FIG. 11 shows the ratio of the accumulating span to a ten-minute period for various insertion angles θ. From the graph shown in FIG. 11, when powders or agglomerates moves in circumferential direction near the inner wall of the container, it can be seen that agglomerates 20 tend to accumulate on the part of the detecting rod 50 facing with the flow if the insertion angle θ of the detecting rod 50 is set within the range from 70 degrees to 170 degrees.

As described above, accumulation of the agglomerates 20 encourages further agglomeration to cause great obstruct of fluidization even including a stop in production. Hence, it is essential to avoid the state in which the rate of accumulation of the agglomerates is particularly high. Specifically, it is essential to avoid inserting the detecting rod 50 at an insertion angle θ within the range from 70 degrees to 170 degrees.

As the results shown in FIGS. 9 through 11, in order to achieve a certain level of sensitivity and resolution with low accumulation of agglomerates 20, the insertion angle θ is preferably set within the range from 20 degrees to 70 degrees, or more preferably within the range from 25 degrees to 50 degrees.

When actually installing the detecting rod 50 in the reactor container 1, the detecting rod 50 is inserted in a nozzle provided diagonally on the outer wall of the reactor container 1. For purposes of construction, the nozzle cannot be provided at an extremely acute angle. From this viewpoint, 20 degrees, as described above, is thought to be a desirable lower limit for the insertion angle θ.

Example for Comparison

A titanium-type catalyst and an alkyl aluminum compound as a co-catalyst were supplied into a gas-phase fluidized-bed olefin polymerization reactor having a diameter of 0.5 meter in a mixed gas atmosphere of ethylene, 1-butene, and hydrogen, and the mixed phase was polymerized.

The detecting rod 50 was inserted at right angles, that is, an insertion angle θ of 90 degrees, and an insertion length of 10 centimeters at a position 8 centimeters above the distributor plate 2. With this configuration, the production of olefin copolymer powder was conducted. Two days after the beginning of production, the first agglomerates were detected in the mixture. One hour later, the mixed phase was not substantially fluidized and the entire mixed phase began to solidify, forcing operations to be shut down. Specifically, since agglomerates adhered to the detecting rod, the mixed phase container was filled with agglomerates as the reaction progressed.

Example of the Present Embodiment

As in the above experiment, a titanium-type catalyst and an alkyl aluminum compound as a co-catalyst were supplied into a gas-phase fluidized-bed olefin polymerization reactor having a diameter of 50 centimeters in a mixed gas atmosphere of ethylene, 1-butene, and hydrogen, and the mixed phase was polymerized.

In this experiment, however, the detecting rod 50 was inserted at an insertion angle θ of 30 degrees and an insertion length of 10 centimeters at a position 8 centimeters above the distributor plate 2. With this configuration, the production of olefin copolymer powder was conducted. Three days after the beginning of production, the first agglomerates were detected. However, the agglomerates did not adhere to the detecting rod. Accordingly, the formed agglomerates were discharged one after another together with the product and production was allowed to continue without any problem.

As described above, according to the present invention, the detecting rod is disposed at an insertion angle ranging from 20 degrees to 70 degrees in relation to the flow of gas and powders. Consequently, the opportunity that agglomerates adhere to the detecting rod can be reduced to increase the sensitivity and precision of detection. Accordingly, it is possible to reduce the accumulation of agglomerates and perform a polymer reaction without obstructing fluidization in the mixed phase container.

Further, according to the present invention, a distributor plate is provided in the bottom of the mixed phase container to force the gas to circulate in a horizontal direction. The detecting rod positioned at a specified height above the distributor plate enables to control the flow of gas and powders in the mixed phase container and effectively to force agglomerates to collide with the detecting rod. Accordingly, agglomerates can be detected with greater sensitivity.

Although certain preferred embodiments of the present invention have been shown and described in detail, it should be understood that various changes and modifications may be made therein without departing from the scope of the appended claims.

What is claimed is:

1. A method for detecting agglomerates in a mixed phase container by measuring strain in a detecting rod disposed in said mixed phase container in which a mixed phase of gas and powders is formed, wherein said detecting rod is disposed at an insertion angle in the range from 20 degrees to 70 degrees with relation to the flow of gas and powders.

2. A method for detecting agglomerates according to claim 1, wherein the detecting rod is disposed horizontally at an insertion angle in the range from 20 degrees to 70 degrees with relation to the flow of gas and powders.

3. A method for detecting agglomerates according to claim 1, wherein a distributor plate is disposed on the bottom of said mixed phase container for diffusing the gas in a horizontal direction, and said detecting rod is positioned at a predetermined height above said distributor plate.

4. An olefin polymerization method, comprising:
   detecting agglomerates in a mixed phase container by measuring strain in a detecting rod disposed in said mixed phase container in which a mixed phase of gas and powders is formed, wherein said detecting rod is disposed at an insertion angle in the range from 20 degrees to 70 degrees with relation to the flow of gas and powders; and
   removing said agglomerates from said mixed phase container.

5. An olefin polymerization method according to claim 4, wherein the detecting rod is disposed horizontally at an insertion angle in the range from 20 degrees to 70 degrees with relation to the flow of gas and powders.

6. An olefin polymerization method, according to claim 4, wherein a distributor plate is disposed on the bottom of said mixed phase container for diffusing the gas in a horizontal direction, and said detecting rod is positioned at a predetermined height above said distributor plate.

7. A method for manufacturing an olefin polymer, said method comprising:

detecting agglomerates in a mixed phase container by measuring strain in a detecting rod disposed in said mixed phase container in which a mixed phase of gas and powders is formed, wherein said detecting rod is disposed at an insertion angle in the range from 20 degrees to 70 degrees with relation to the flow of the gas and powders; and removing said agglomerates from said mixed phase container.

8. A method for manufacturing an olefin polymer according to claim 7, wherein the detecting rod is disposed horizontally at an insertion angle in the range from 20 degrees to 70 degrees with relation to the flow of gas and powders.

9. A method for manufacturing an olefin polymer according to claim 7, wherein a distributor plate is disposed on the bottom of said mixed phase container for diffusing the gas in a horizontal direction, and said detecting rod is positioned at a predetermined height above said distributor plate.

10. A method for detecting agglomerates according to claim 1, wherein the powders contain products of olefin polymer and/or catalysts.

* * * * *